United States Patent
Fleming (10) Patent No.: US 6,809,648 B1
(45) Date of Patent: Oct. 26, 2004

(54) AERIAL SAMPLER SYSTEM

(75) Inventor: Rex J. Fleming, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 60 days.

(21) Appl. No.: 10/304,577

(22) Filed: Nov. 26, 2002

(51) Int. Cl.[7] .................................................. G01W 1/00
(52) U.S. Cl. ....................... 340/601; 340/962; 340/966; 340/968; 73/861.07
(58) Field of Search .............................. 340/601, 962, 340/966, 968, 581, 583, 580; 73/861.07, 170.02

(56) References Cited

U.S. PATENT DOCUMENTS

| | | | | |
|---|---|---|---|---|
| 2,970,475 A | * | 2/1961 | Werner | 374/138 |
| 5,302,026 A | * | 4/1994 | Phillips | 374/135 |
| 5,544,526 A | * | 8/1996 | Baltins et al. | 73/180 |
| 5,653,538 A | * | 8/1997 | Phillips | 374/138 |
| 5,731,507 A | * | 3/1998 | Hagen et al. | 73/182 |
| 6,070,475 A | * | 6/2000 | Muehlhauser et al. | 73/861.68 |
| 6,076,963 A | * | 6/2000 | Menzies et al. | 374/138 |
| 6,250,149 B1 | * | 6/2001 | Black | 73/178 R |
| 6,269,320 B1 | * | 7/2001 | Otto | 702/127 |
| 6,609,825 B2 | * | 8/2003 | Ice et al. | 374/138 |
| 6,672,152 B2 | * | 1/2004 | Rouse et al. | 73/170.02 |

\* cited by examiner

*Primary Examiner*—Daniel J. Wu
*Assistant Examiner*—Sihong Huang
(74) *Attorney, Agent, or Firm*—Duft Setter Ollila & Bornsen PLLC (57) ABSTRACT

An aerial sampler system includes an enclosure, a transfer system, and a measurement system. The enclosure is connected to an external surface of an aerial vehicle and receives atmospheric flow from the external surface of the aerial vehicle. The enclosure also directs at least some of the atmospheric flow into an aperture in the external surface. The transfer system transfers some of the atmospheric flow from the aperture to a measurement system. The measurement system is internal to the external surface of the aerial vehicle and measures atmospheric trace gases in the atmospheric flow.

28 Claims, 8 Drawing Sheets

*FIG. 1*

PRIOR ART

AERIAL SAMPLER SYSTEM

RELATED APPLICATIONS

Not applicable

FEDERALLY SPONSORED RESEARCH OR DEVELOPMENT

This invention was made with Government support under Contract number #DTFA01-97-C-00006 awarded by the Federal Aviation Administration. The Government has certain rights in this invention.

MICROFICHE APPENDIX

Not applicable

BACKGROUND OF THE INVENTION

1. Field of the Invention

The invention is related to the field of aviation and weather related applications, and in particular, to apparatuses and methods for an aerial sampler system.

2. Description of the Prior Art

Aircraft have typically used two fundamental types of air samplers. The first type is called a total air temperature (TAT) probe that obtains total (dynamic) air temperature and static (ambient) air temperature. This TAT probe extends from the aircraft skin about 3 inches, which is away from the friction-heated boundary layer of air next to the aircraft's metal surface. The TAT probe measures the dynamic (total) temperature and obtains the static temperature through the equation:

$$T_T = T_S(1+0.2M^2)$$

where $T_T$ is the total temperature;
  $T_S$ is the static temperature; and
  M is the Mach number which is the fractional speed of the aircraft relative to the speed of sound.

The TAT probe includes a probe heater, which is an FAA requirement due to icing concerns. One problem is the heater tends to fail, which is the highest failure mode of the probes.

The second type of probe is called a pitot tube and is used to measure differential pressure (total minus static) for subsequent calculation of aircraft velocity through Bernoulli's equation:

$$V^2 = 2(P_T - P_S)/\rho$$

where V is velocity;
  $P_T$ is total pressure;
  $P_S$ is static pressure; and
  $\rho$ is the density of air, which is a function of atmospheric pressure and temperature.

These two probes work together to provide the information needed for efficient flight. Both types of probes have the common feature of extending away from the airframe to avoid contaminated measurements induced by boundary layer effects near the aircraft's skin. One problem with these two probes is the frictional drag from the extension of both probe from the aircraft's skin. The TAT probe has a frictional drag that is an effective 2.5 lbs. Over time, the cost of additional fuel for such additional weight ranges from $1–$2 per pound per week per aircraft. Another problem arises when the probes are applied to stealth aircrafts. Both of the probes increase the radar cross section, which increases the radar visibility of the aircraft.

Another important measurement for aircraft is water vapor. Water vapor affects virtually all aspects of aviation weather and thus, the safety, efficiency, and capacity of an airspace system. For example, summertime convection is behind most traffic delays. Weather prediction in general, but especially precipitation and severe storm prediction, are crucially dependent upon accurate water vapor profiles in the lower troposphere. The commercial aircraft real-time ascent and descent reports can provide profiles of winds, temperature, and water vapor.

Figure 1:
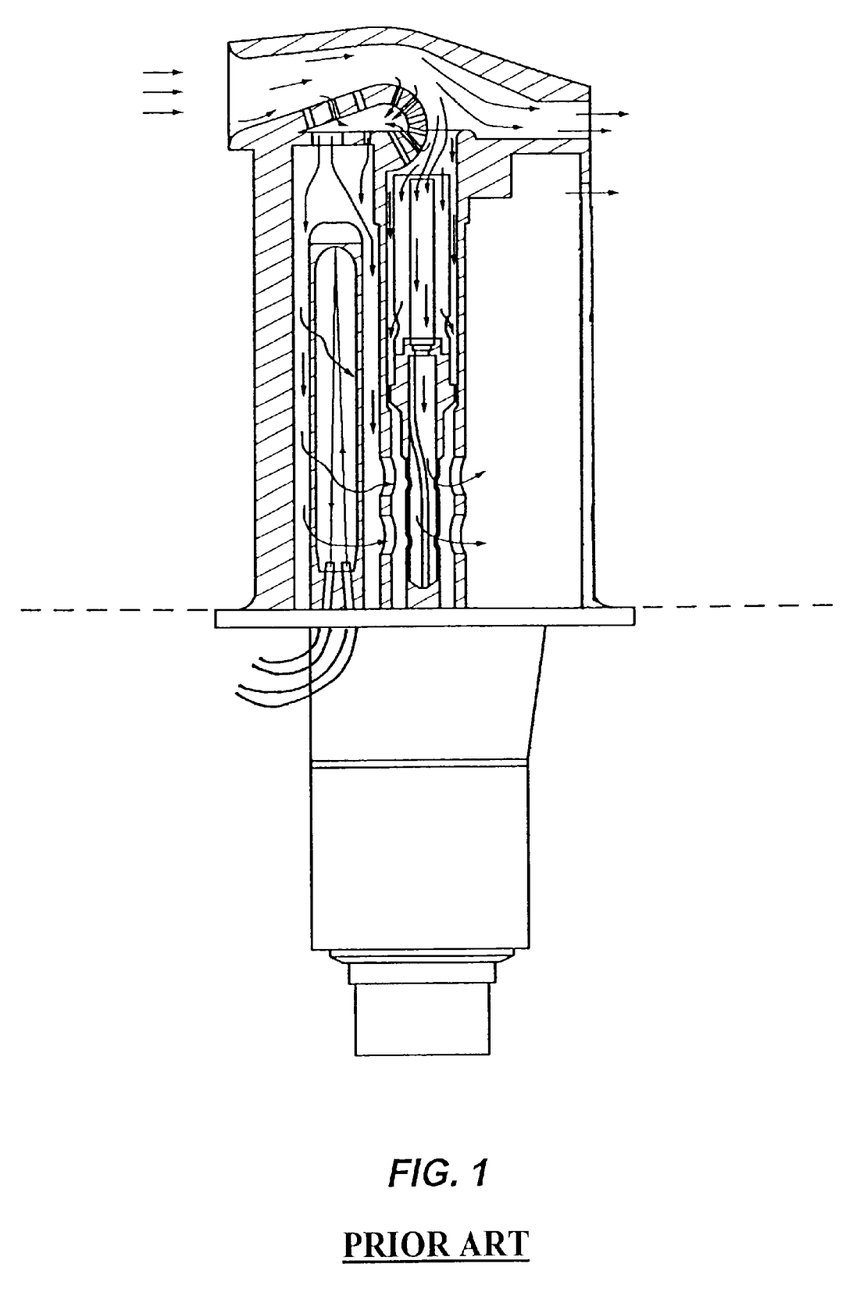
FIG. 1 is an illustration of a prior system with a total air temperature probe and a water vapor sensing system in the prior art.

One prior system has used the TAT probe in combination with a water vapor sensing system. FIG. 1 depicts a prior system with the TAT probe and a water vapor sensing system in the prior art. The prior system includes a standard TAT probe to measure total air temperature and static air temperature from the air flow. The water vapor sensing system includes a diode laser to measure the water vapor. This prior system was tested in a prototype mode but never built as a commercial product because of the limited space available within the TAT probe. This forced the use of fiber optic cables to carry the laser light and these induced optical "fringes" that reduced sensitivity of the diode laser measurement technique.

Another prior system uses an "open path" for diode lasers to measure water vapor. The laser transmitter and receiver are external to the aircraft. However, this prior system has accuracy and solar interference problems in addition to the drag concerns.

SUMMARY OF THE INVENTION

The inventions solve the above problems by using an aerial sampler system. The aerial sampler system includes an enclosure, a transfer system, and a measurement system. The enclosure is connected to an external surface of an aerial vehicle and receives atmospheric flow from the external surface of the aerial vehicle. The enclosure also directs at least some of the atmospheric flow into an aperture in the external surface. The transfer system transfers some of the atmospheric flow from the aperture to a measurement system. The measurement system is internal to the external surface of the aerial vehicle and measures atmospheric trace gases in the atmospheric flow.

In some embodiments, the measurement system measures water vapor in the atmospheric flow. In some embodiments, the measurement system includes a laser transmitter, a receiver, and a processing system that determines water vapor based on the received laser signals. In some embodiments, the laser transmitter is a diode laser transmitter. In other embodiments, the laser transmitter is a quantum cascade laser transmitter. In some embodiments, the measurement system includes a temperature sensor and a pressure sensor. In some embodiments, the enclosure includes an inertial separator that converges and diverges the atmospheric flow. In some embodiments, the enclosure includes a pressure sensor that determines pressure for ice detection. In some embodiments, the enclosure includes electrically heated metal that removes ice.

BRIEF DESCRIPTION OF THE DRAWINGS

The same reference number represents the same element on all drawings.

DETAILED DESCRIPTION OF THE PREFERRED EMBODIMENT

FIGS. 2–8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 2:
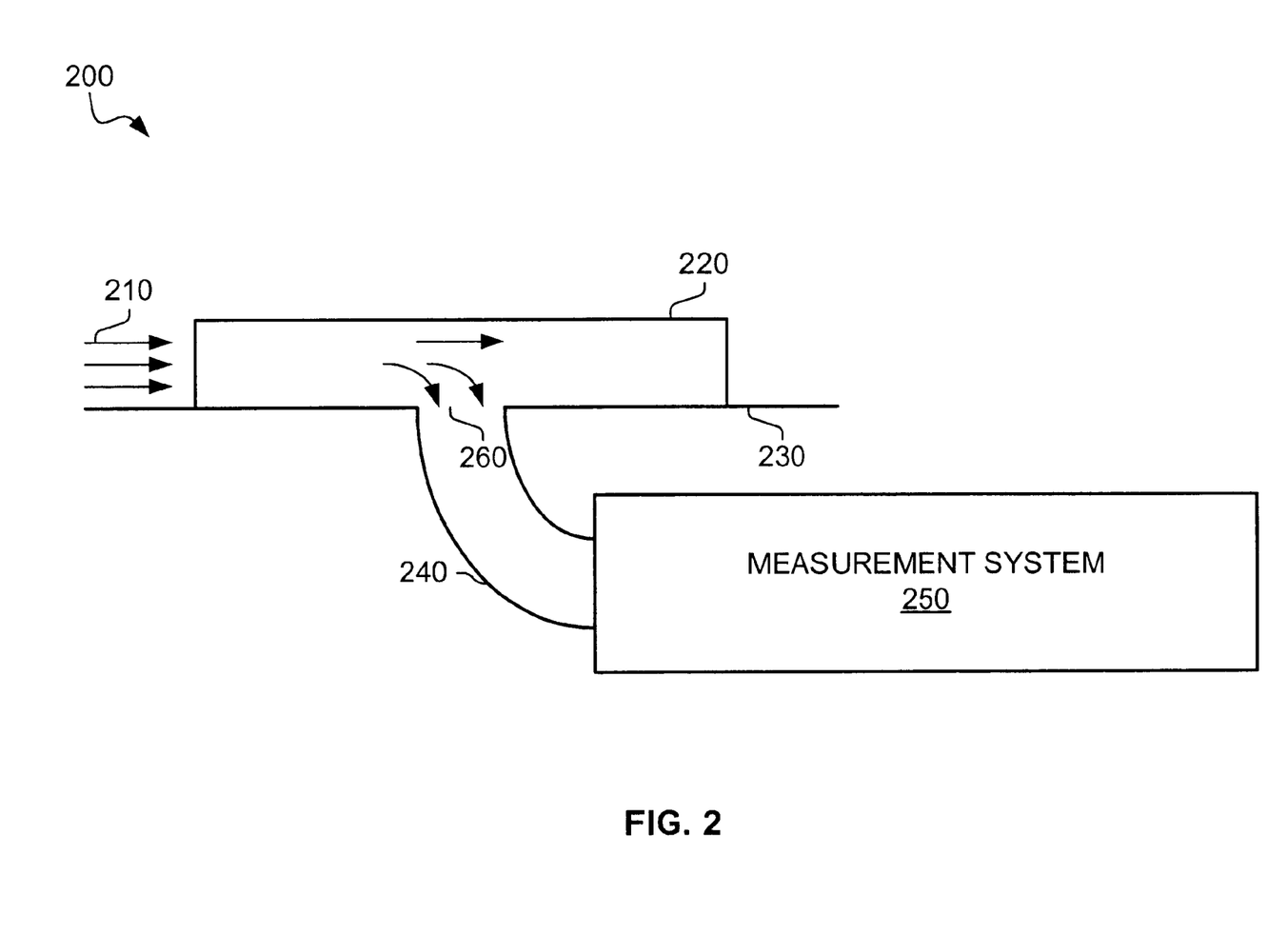
FIG. 2 is an illustration of an aerial sampler system in an example of the invention.
Figure 3:
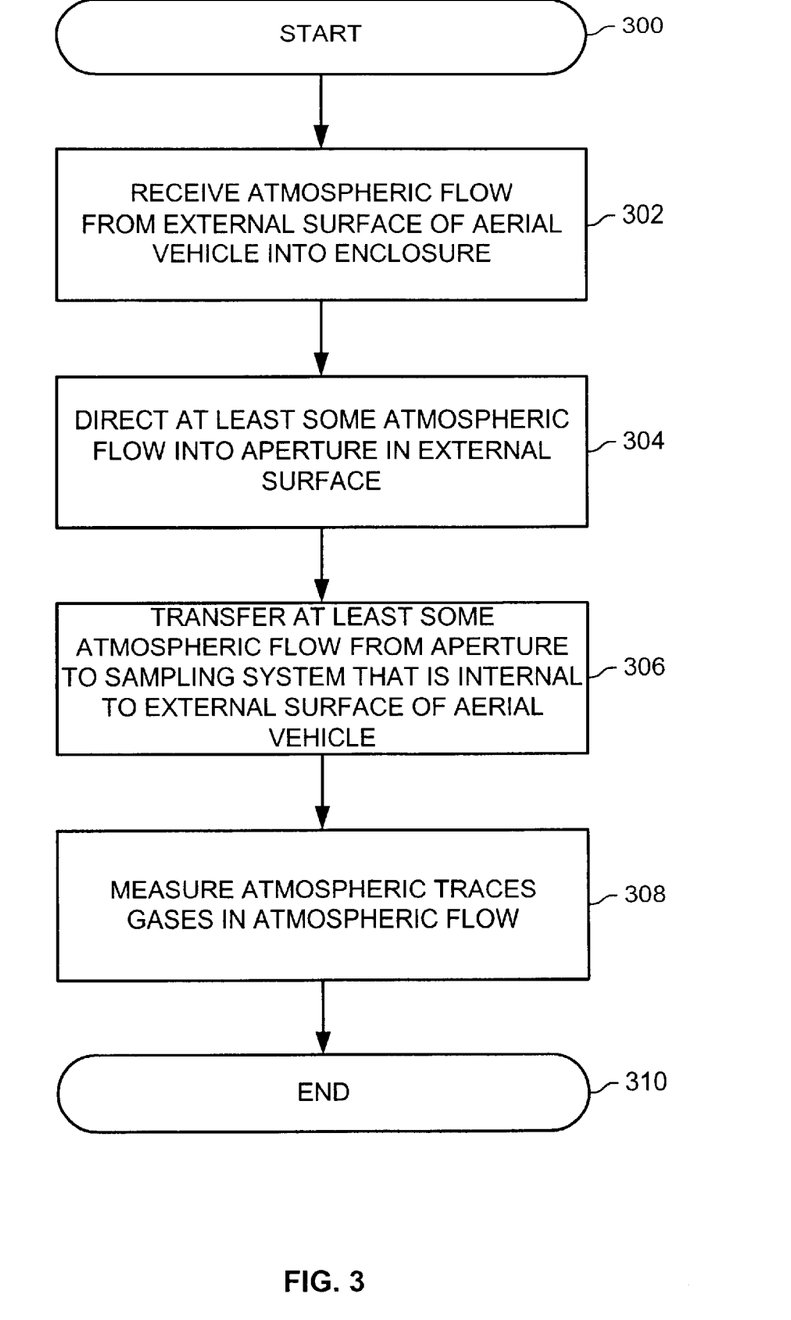
FIG. 3 is a flow chart of an aerial sampler system in an example of the invention.

Aerial Sampler System—FIGS. 2–3

FIG. 2 depicts an aerial sampler system 200 in an example of the invention. The aerial sampler system 200 includes an enclosure 220, an external surface 230 of an aerial vehicle, a transfer system 240, and a measurement system 250. The enclosure 220 is located on the external surface 230 of the aerial vehicle. The external surface 230 has an aperture 260. At the aperture 260, the transfer system 240 is connected to the enclosure 220 and the external surface 230 to allow atmospheric flow 210 to enter the transfer system 240. The transfer system 240 is also connected to the measurement system 250.

The atmospheric flow 210 is any flow of trace gases and/or particles that are in a planetary atmosphere. The atmospheric flow 210 typically contains water vapor, which is a trace gas and can vary from 3 to over 40,000 parts per million by volume (ppmv). In one example of the earth's atmosphere, the atmospheric flow contains nitrogen and oxygen gas, water vapor, other trace gases, and particles including aerosols, possible liquid water droplets, and ice crystals. The external surface 230 of an aerial vehicle is the outer layer of an aerial vehicle. In one example, the external surface 230 is the "skin" of a commercial jet aircraft. An aerial vehicle is any object that flies. Some example of aerial vehicles are commercial and military jet aircraft, special purpose manned aircraft, and unmanned aerial vehicles (UAVs).

An enclosure 220 is any configuration of materials that is configured to receive the atmospheric flow 210 from an external surface 230 of an aerial vehicle and direct at least some of the atmospheric flow 210 into an aperture 260 in the external surface 230. One embodiment of the enclosure 220 forms a rib that is shown in FIGS. 4, 5, 6, and 7, which are described below. The transfer system 240 is any device, group of devices, or material that is configured to transfer some of the atmospheric flow 210 from the aperture 260 of an external surface of an aerial vehicle to a measurement system 250. One example of the transfer system 240 is a coupling pipe, which is described below in FIGS. 6, 7, and 8.

Figure 6:
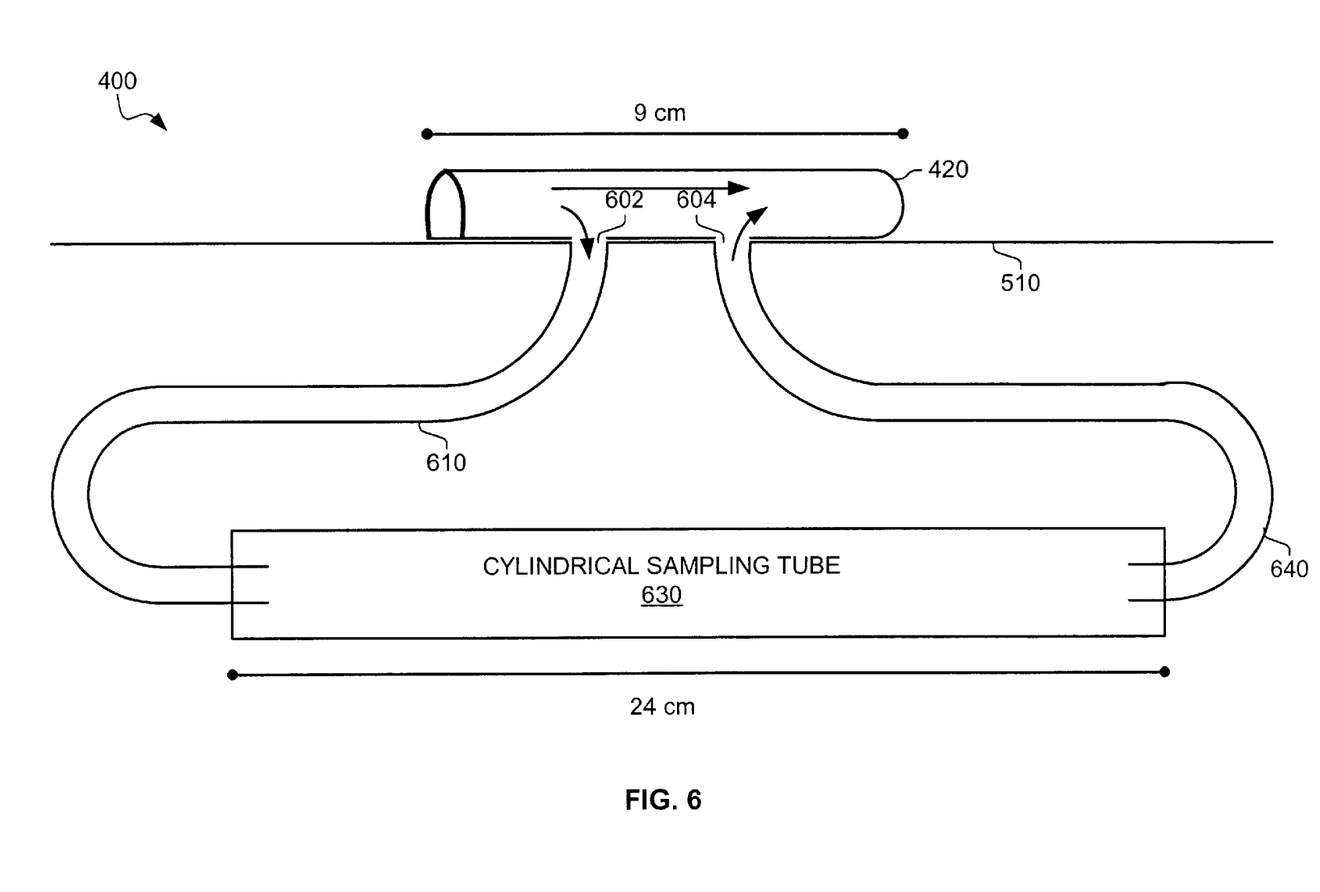
FIG. 6 is an illustration of a side view of the FS system in an example of the invention.
Figure 8:
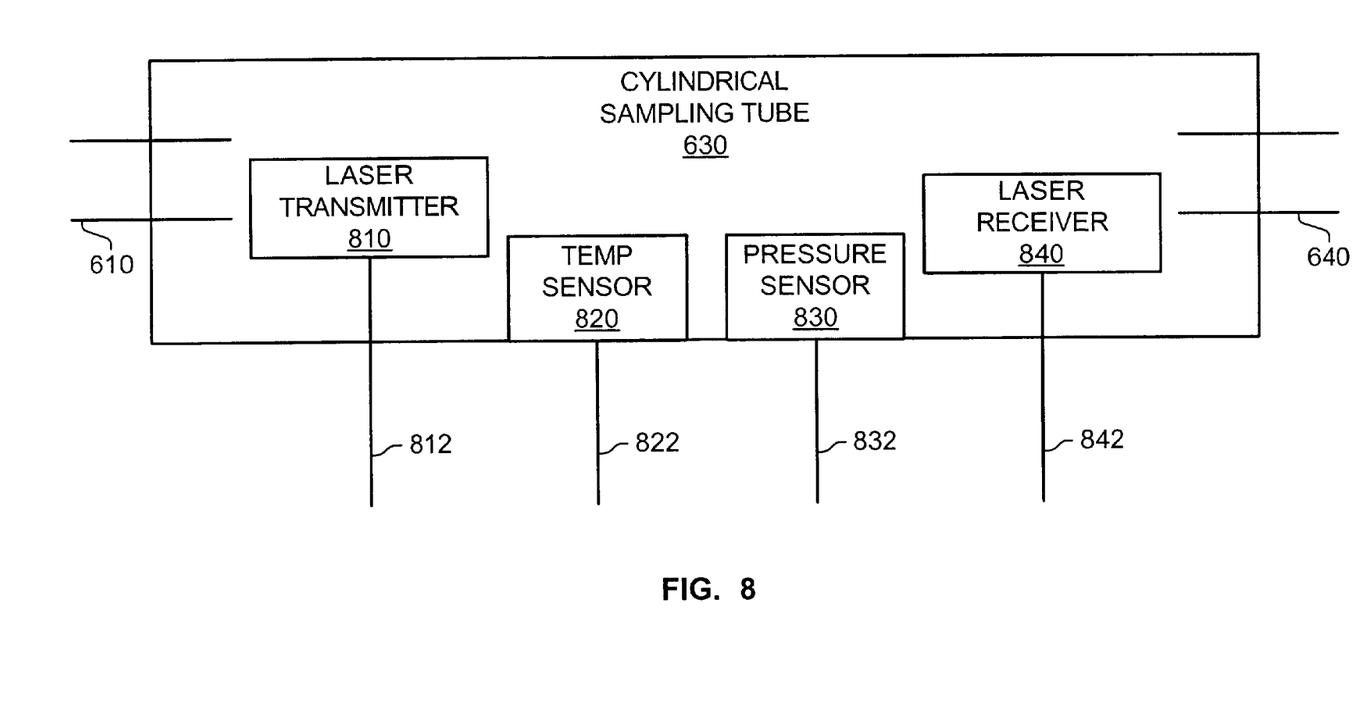
FIG. 8 is an illustration of a cylindrical sampling tube in an example of the invention.

The measurement system 250 is any device, group of devices, or material configured to measure atmospheric trace gases of the atmospheric flow and is internal to an external surface of an aerial vehicle. One example of the measurement system 250 is a cylindrical sampling tube which is shown in FIGS. 6 and 8, which are described below. An example of measuring atmospheric water vapor is described below.

FIG. 3 depicts a flow chart of the aerial sampler system 200 in an example of the invention. FIG. 3 begins in step 300. In step 302, the enclosure 220 receives the atmospheric flow 210 from the external surface 230 of an aerial vehicle. In step 304, the enclosure 220 directs some of the atmospheric flow 210 into the aperture 260 in the external surface 230. In step 306, the transfer system 240 transfers some of the atmospheric flow 210 from the aperture 260 to the measurement system 250 that is internal to the external surface 230 of the aerial vehicle. In step 308, the measurement system 250 measures the atmospheric trace gases of the atmospheric flow 210. FIG. 3 ends in step 310.

The aerial sampler system 200 advantageously measures atmospheric flow from the skin of the aerial vehicle. The aerial sampler system 200 has minimal frictional drag as compared with the TAT probe and the pitot probe. Also, the aerial sampler system 200 does not include any heater as in the TAT probe, which reduces cost, weight, energy consumed, and maintenance for failures. Further advantages for other embodiments are discussed below.

Fleming Sampler System—FIGS. 4–8

Figure 4:
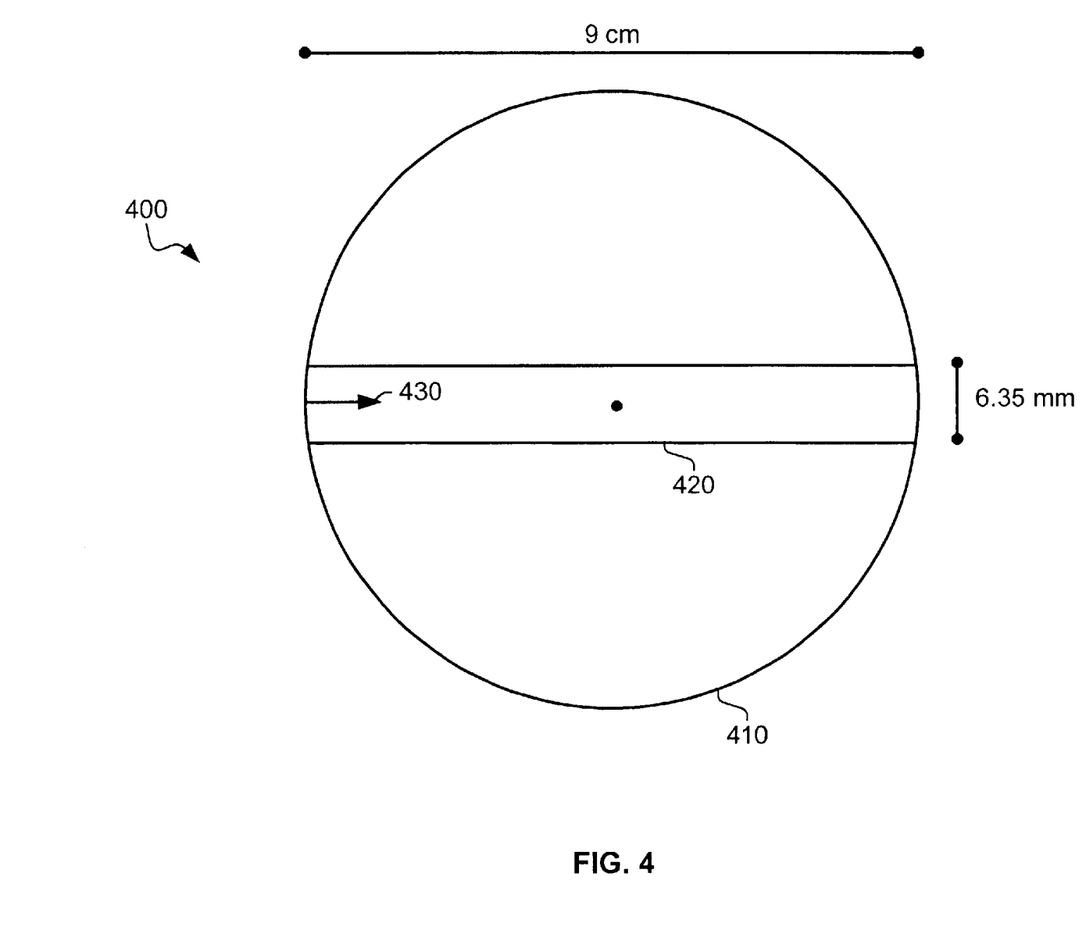
FIG. 4 is an illustration of a top view of an enclosure in the Fleming Sampler (FS) system in an example of the invention.

FIG. 4 depicts a top view of an enclosure in a Fleming Sampler (FS) system 400 in an example of the invention. The FS system 400 includes an enclosure 410 that forms a rib 420 on the bottom side of the enclosure. Typically, the rib 420 is not seen from the top view but is shown in FIG. 4 to show the placement of the rib 420 within the enclosure 410. In this embodiment, the enclosure 410 is attached on top of an external plate that has a diameter of approximately 9 cm and the external plate is not shown in FIG. 4. In this embodiment, the enclosure 410 and the external plate are circular. In other embodiments, the enclosure 410 and the external plate could have another shape. The external plate is a metal doubler plate of standard thickness conventionally attached to an airframe. The external plate has two 0.635 cm holes [¼ inch] leading to the interior of the aircraft. The rib 420 has a width of 6.35 mm and a length of approximately 9 cm. The rib 420 extends from left to right across the center of the external plate. In this example, the aircraft is assumed to be moving from right to left. Thus, the air is entering the left side of the rib 420 and exiting the right side or tail of the rib 420. The direction of the air is shown by the arrow 430.

Figure 5:
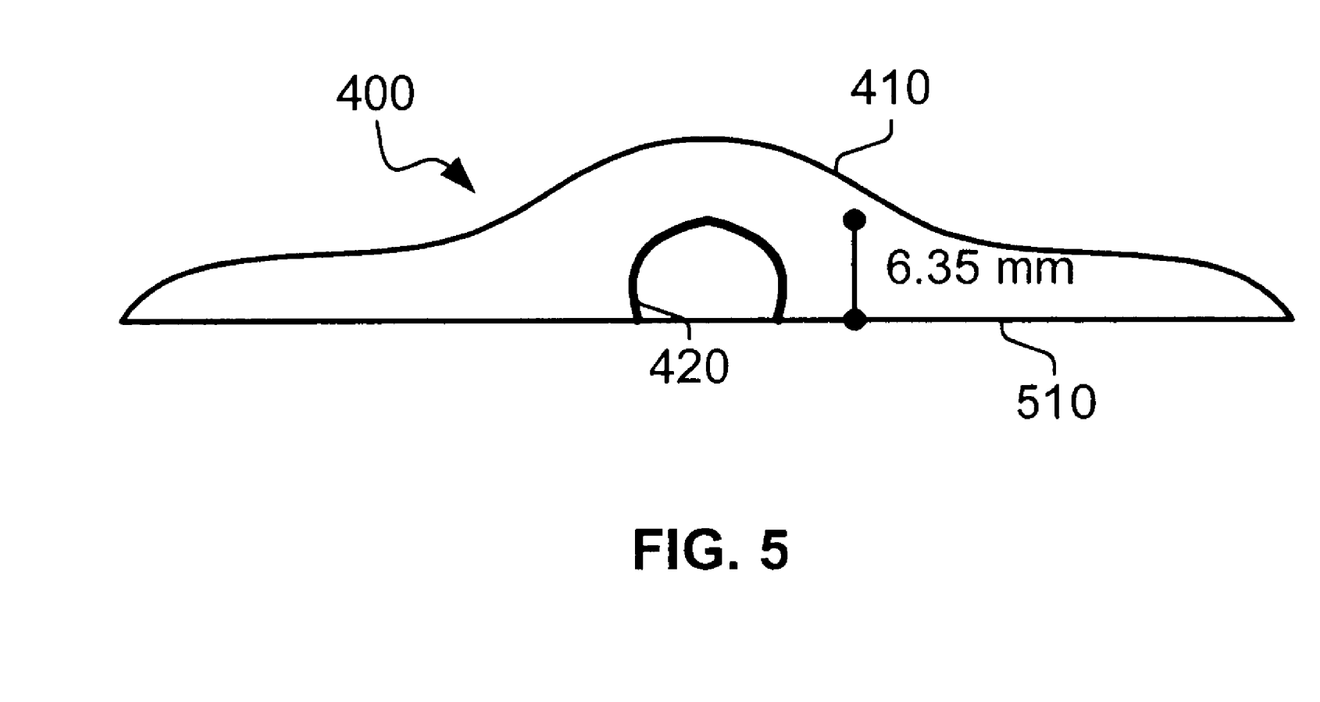
FIG. 5 is an illustration of a cross section view of an enclosure in the FS system in an example of the invention.

FIG. 5 depicts a cross section view of the enclosure 410 of the FS system 400 in an example of the invention. FIG. 5 depicts the rib 420 located within the enclosure 410, which is attached on top of the external plate 510. In this embodiment, the diameter of the rib 420 is slightly tapered to achieve inertial separation of particles (liquid water droplets, ice crystals, aerosols, etc.) out the tail of the rib 420. The rib 420 has a height of approximately 6.35 mm.

FIG. 6 depicts a side view of FS system 400 in an example of the invention. The FS system 400 includes a rib 420, an external surface 510 of the aircraft, an incoming coupling pipe 610, a cylindrical sampling tube 630, and an outgoing coupling pipe 640. The external plate is not depicted in FIG. 6 for the sake of simplicity and to focus on the flow of atmospheric trace gases to be measured. The rib 420 is attached to the external surface 510 of the aircraft via the external plate. The rib 420, the external plate, and the external surface 510 of the aircraft has an incoming hole 602 and an outgoing hole 604 for air flow. The incoming coupling pipe 610 is connected to the rib 420, the external plate, and the external surface 510 through the incoming hole 602. The opposite end of the incoming coupling pipe 610 is connected to the cylindrical sampling tube 630. The cylindrical sampling tube 630 is also connected to the outgoing coupling tube 640. The outgoing coupling tube 640 is connected to the rib 420, the external plate, and the external surface 510 of the aircraft through the outgoing hole 604.

In this embodiment, the incoming coupling pipe 610 and the outgoing coupling pipe 640 are stainless steel, flexible Kevlar hoses or other hoses of similar material whether fixed or flexible that direct air flow into and out of the cylindrical sampling tube 630. In some embodiments, the incoming coupling pipe 610 and the outgoing coupling pipe 640 may be heated or non-heated. In this embodiment, the cylindrical sampling tube 630 is a stainless steel tube that is 24 cm long. In this embodiment, the cylindrical sampling tube 630 is optimized for an existing diode laser for water vapor measurement, which is described in further detail below in FIG. 8. In another embodiment, the cylindrical sampling tube 630 is 12 cm long with a sapphire-coated mirror at the end that keeps the effective path length 24 cm long. In other embodiments, other reflective material could be in the cylindrical sampling tube 630 to decrease the path length. The diameter of the inlets of the rib 420, the location of the apertures, and the diameter of the cylindrical sampling tube 630 can be altered for other embodiments and optimized for a particular aerial application.

Figure 7:
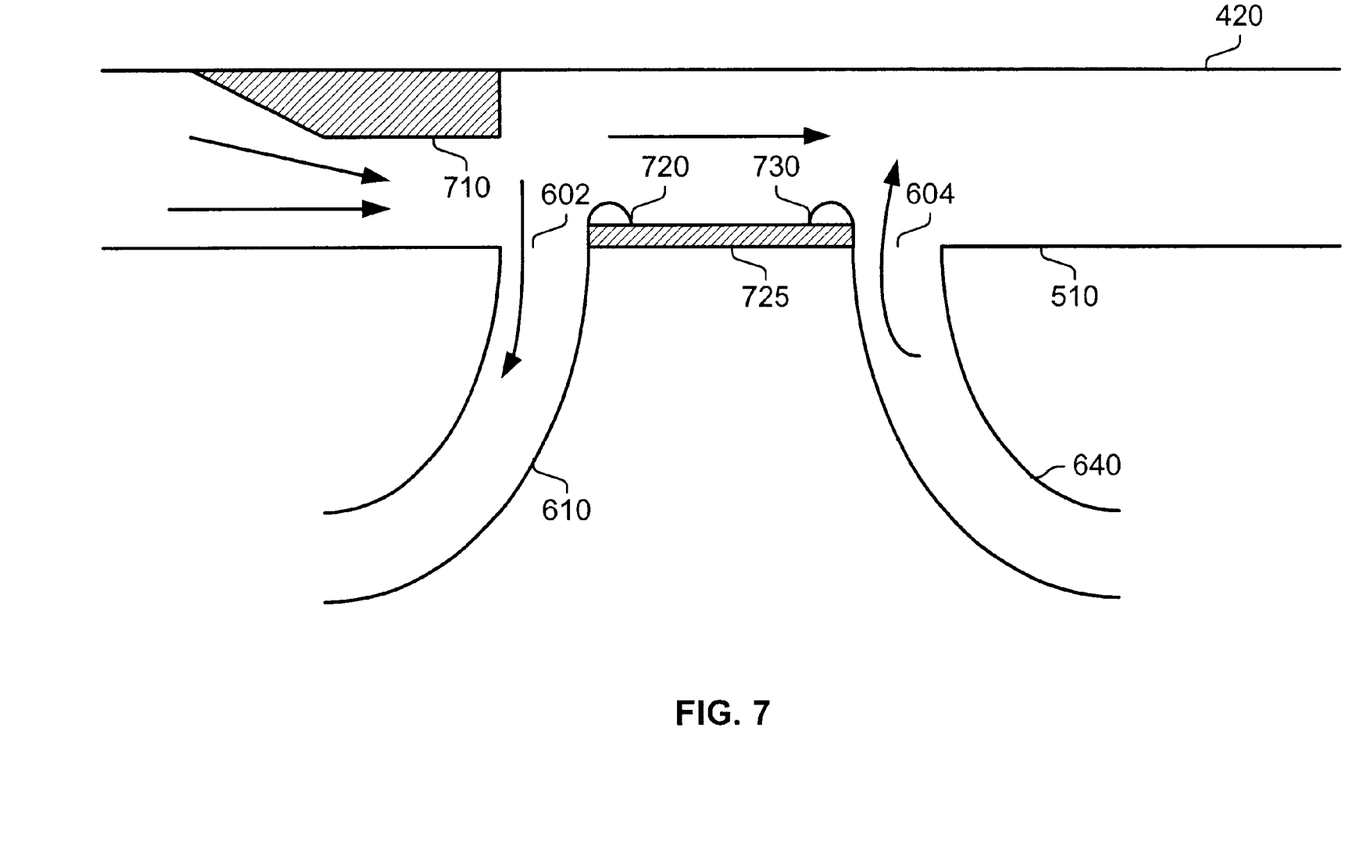
FIG. 7 is an illustration of a detailed side view of the rib of the enclosure, an incoming coupling pipe, and an outgoing coupling pipe in an example of the invention.

FIG. 7 depicts a detailed side view of the rib 420, the incoming coupling pipe 610, and the outgoing coupling pipe 640 in an example of the invention. The rib 420 includes an inertial separator 710. The inertial separator 710 is attached to the top of the rib 420. The inertial separator 710 is a converging metal shape with an approximately 1–2 mm rise. Once again, in this example, the air flows left to right in the rib 420. The inertial separator 710 is configured to converge air flow. The air flow then diverges after the inertial separator 710. The inertial separator 710 forces most particles out the back exit of the rib 420 because of the momentum of the particles (the combination of their density and the fast flow). In other embodiments, there are numerous variations in the height, shape, and position of the inertial separator 710 to converge and then diverge air flow. Also, in other embodiments, the outgoing coupling pipe 640 is attached in various configurations in the aerial vehicle to remove the sampled atmospheric flow from the cylindrical sampling tube 630.

In some embodiments, the rib 420 may include an incoming flow enhancer 720, an outgoing flow enhancer 730, and a base flow enhancer 725. The incoming flow enhancer 720 on top of the base flow enhancer 725 is adjacent to the incoming hole 602. The incoming flow enhancer 720 and the base flow enhancer 725 assist in directing air flow in the incoming hole 602 to the incoming coupling pipe 610. The outgoing flow enhancer 730 on top of the base flow enhancer 725 is adjacent to the outgoing hole 604. The outgoing flow enhancer 730 and the base flow enhancer 725 assist in directing air flow out of the outgoing hole 604 from the outgoing coupling pipe 640. The outgoing flow enhancer 730 and the base flow enhancer 725 prevent the air flow from outgoing hole 604 from going right to left in the opposite direction of the original air flow.

FIG. 8 depicts an illustration of the cylindrical sampling tube 630 in an example of the invention. As discussed above, the cylindrical sampling tube 630 is connected to the incoming coupling pipe 610 and the outgoing coupling pipe 640. The cylindrical tube 630 comprises a laser transmitter 810, a temperature sensor 820, a pressure sensor 830, and a receiver 840.

The cylindrical sampling tube 630 is 24 cm long. This length is sufficiently long for extremely accurate water vapor mixing ratios such as measurements of equivalent relative humidity (RH) as dry as 5% at 40,000 feet. The length is also sufficiently short for the fast-moving air to provide a new sampling volume in a small to large fraction of a second depending upon the aircraft speed. The cylindrical sampling tube 630 also comprises a temperature sensor 820 and a pressure sensor 830 for measuring temperature and pressure, respectively. The temperature sensor 820 and the pressure sensor 830 are mounted on the chamber walls of the cylindrical sampling tube 630. The laser transmitter 810 is a conventional diode laser transmitter configured to transmit laser signals. The receiver 840 is a conventional receiver configured to receive laser signals. In other embodiments, the laser transmitter 810 can be a quantum cascade laser. Measurements of water vapor by diode lasers is disclosed in a publication entitled "Open-Path, Near-Infrared Tunable Diode Laser Spectrometer for Atmospheric Measurement for $H_2O$," by May, R. D., in *the Journal for Geophysical Research*, vol. 103, p. 19,161–19,172 (1998), which is hereby incorporated by reference.

The links 812, 822, 832, and 842 are connected to the laser transmitter 810, the temperature sensor 820, the pressure sensor 830, and the laser receiver 840, respectively. In some embodiments, the links 812, 822, 832, and 842 are connected through a multi-pin connector. In some embodiments, the links 812, 822, 832, and 842 are connected to electronic circuitry, computers, or other processing systems that control, manage and/or process the measurements from the laser transmitter 810, the temperature sensor 820, the pressure sensor 830, and the laser receiver 840. These electronic circuitry, computers, or other processing systems could be located anywhere within the aerial vehicle. Processed information can then be sent to the cockpit and/or to the ground via wireless communications. The measurements could be used in a variety of applications including weather related applications and navigation.

The mixing ratio of atmospheric trace gases may be sampled from the boundary layer of the aircraft because the ultimate intended measurement is unaffected. The laser signal is at a chosen frequency that matches the absorption cross section frequency of the trace gas being measured. Thus, the mixing ratio of water vapor or of some other trace gas can be accurately determined from the lasers, the use of Beer's Law, and measurement of pressure and temperature. It is the measurement of the actual temperature and pressure near the laser light path that makes Beer's law useful. The mixing ratios are conserved properties whether they be determined in static conditions, in fully dynamic or total conditions, or in conditions between the two extremes. Beer's law is:

$$I = I_o \exp(-\sigma n\, l)$$

where I is light intensity at the detector (receiver);
  $I_o$ is the light source intensity; and
  ($\sigma n\, l$)=absorbance
    where $\sigma$ is the molecular absorption cross section (a function of frequency, pressure, and temperature);
    n is the number density of the absorbing species to be measured such as $H_2O$, $CO$, $CH_4$, $N_2O$, $NO$, $SOx$, $O_3$; and
    l is the path length.

Aerial vehicles may encounter rain, snow, or dense cloud events (water droplets, ice crystals, or a mixture of both) that lead to sensor "wetting." This FS system 400 and the use of a specific laser frequency have a distinct advantage in not being affected by the liquid and solid water elements as such elements do not absorb the laser light at the selected frequency. Only if there were significant amounts of such elements in the cylindrical sampling tube 630 (a situation avoided by the use of the inertial separator 710 in the rib 420 of the FS system 400) would they affect the laser light scattering (not the light absorption) and reduce the sensitivity of the measurement.

In other embodiments, other sampling tubes are added in series to the cylindrical sampling tube 630 so that quantum cascade laser simultaneously measures various chemical or biological species with a different path length that is optimized to match the desired measurement range and consistent with the quantum cascade laser frequency and efficiency.

In one embodiment for an unmanned aerial vehicle such as the large RQ-4A Global Hawk that flies up to 65,000 ft, the FS system 400 measures the water vapor in the stratosphere to a minimum value of 3 ppmv. The usual range in the driest part of the tropical lower stratosphere is typically 3–5 ppmv. In this embodiment, the cylindrical sampling tube 630 is extended to 40 cm.

In another embodiment on the opposite end of the current spectrum of unmanned aerial vehicles such as the small GNAT 750 that has an altitude flight limit of 25,000 feet, the FS system 400 includes the cylindrical sampling tube that is 10 cm. This embodiment accurately measures the full range of expected water vapor mixing ratio values or equivalent RH encountered in the troposphere below 25,000 feet.

In other embodiments, the aircraft could be any unmanned aerial vehicle that operates below 18,000 ft. In this embodiment, the dimensions of the FS system 400 is scaled down by a factor of two except for the length of the cylindrical sampling tube, which is scaled down by a factor of five to ten such as with a path length of 4 to 2 cm. This embodiment achieves a minimum measurement of 1% RH at 18,000 ft. and lower minimum values yet at lower levels of the troposphere.

The FS system 400 has the following advantages. First, the FS system 400 does not include the heater from the TAT probe, which eliminates the costs, weight, energy consumption, and failures associated with the TAT probe. The FS system 400 also has reduced frictional drag as compared with the TAT probe and pitot tube. This may save $1–$2 per pound per week per aircraft, which is a significant cost.

The FS system 400 is also lightweight and efficient as compared to the "open path" prior system. The FS system 400 provides an environment for more accurate measurements of atmospheric trace gases. Also, the FS system 400 does not have the problems of solar interference as in the "open path" prior system. Also, the FS system 400 has less frictional drag than the "open path" prior system.

The FS system 400 also has more sensitivity than the prior system with the TAT probe and the water vapor sensing system by a factor of more than six. This occurs because of the added width and length of the cylindrical sampling tube 630. This eliminates the need for fiber optic laser connections and thus fringes. The measured minimum absorbance improves from $1\times10^{-4}$ to $3.75\times10^{-5}$—a factor of 2.67 improvement in sensitivity. The added length of the cylindrical sampling tube 630 to 24 cm from 10.2 cm increases the path length by a factor of 2.35. Together, these factors multiply to an improved sensitivity of a factor of 6.2.

The FR system 400 and the use of lasers allows a highly effective water vapor measurement system that can have a significant impact on improving aviation safety, efficiency, and capacity. The FS system 400 and the use of lasers allows water vapor and other trace gas measurements that can contribute to atmospheric science across a spectrum of atmospheric science application ranging from short-term weather predictions to climate change assessments.

The laser light produces accurate water vapor answers even in the presence of aerosols unless the density and number of such aerosols is exceedingly large. If this occurs, the laser intensity (a separate measurement) drops and the software can use information from a second cross cell laser to verify such a condition. These and similar procedures can be shown to lead to further benefits of the FS system 400 in providing an early warning system for volcanic ash (a serious concern for engine performance and hence, safety).

Another application for the FS system 400 is for nuclear-biological-chemical (NBC) terrorism. Mesoscale information from commercial aircraft as part of a composite environmental observing system help mitigate the effects of NBC terrorism. Diode and QC lasers in the FS system 400 provide valuable information for the strategic mesoscale observing system that is now unavailable, and on the tactical observing system that is brought to ground zero should an NBC terrorism event occur. Accurate analysis of atmospheric stability (temperature and water vapor) are required to properly drive plume models. The commercial aircraft can help provide 100 times more stability profiles per day than obtainable from today's balloon-borne radiosonde system. This is the strategic observing system prior to an event. The nature of the tactical observing system is driven by the form of the NBC terrorism event. The identification of the contaminated plume and the environment surrounding it at ground zero can be obtained with special manned aircraft and UAVs with the FS system 400. This would be an important part of the tactical observing system.

In one embodiment for an icing detector, the inlet to the enclosure is made sufficiently small that an icing situation would immediately block the flow into the enclosure. The inertial separator in the enclosure is not needed and is replaced with a pressure sensor. The pressure sensor (which normally would detect full dynamic pressure) would only detect the much weaker static pressure if the hole was blocked by ice build-up. Thus, the detection of ice is performed instantaneously.

The second function of a successful icing detector is to remove the ice extremely rapidly in order to again serve as an icing detector. The time required to remove the ice is what determines the sensor's response time. Of the two known types of icing sensors in use or being developed today, this response time is exceedingly slow (20 or more seconds). The area of ice capture is too large in these sensors and it takes too long to remove the ice through electrical resistance heating. Thus, these sensors have little value in ascent/descent of an aircraft where one would like to know the vertical levels of icing more precisely.

In this embodiment, the enclosure inlet has a thin ring of electrically heated metal surrounding the inlet orifice. This large heat source confined to the miniature ringlet provides a response time of less than 1–2 seconds or a factor of 10 faster than current icing sensors. The sensor information would pass from the enclosure via a multiple pin connector to an external processing system. The processing system includes the heating circuit logic. Heating begins upon ice detection and an immediate cease of heating upon ice removal (pressure back to full dynamic pressure). From the processing system, the information is relayed to the cockpit and to the ground-based personnel in real time like the other application embodiments.

In one embodiment for volcanic ash, the cylindrical sampling tube 630 includes a laser detecting gas from a volcanic eruption and another simple optical laser looking across the cylindrical sampling tube that would confirm that the volcanic aerosol content was sufficiently high. Normally, the inertial separator would remove most aerosol particles-but in a volcanic eruption incident the aircraft may come close enough to the volcanic plume, or to the plume in its subsequently dispersed form, such that the concentration of aerosol particles would be sufficiently dense to override the effects of the inertial separator-leaving a detectable signal. The sensor information would pass from the cylindrical sampling tube 630 via a multiple pin connector and go to an external processing system. From the processing system, the information is relayed to the cockpit and to the ground-based personnel in real-time like the other application embodiments of the invention.

What is claimed is:

1. An aerial sampler system comprising:
   an enclosure connected to an external surface of an aerial vehicle and configured to receive atmospheric flow from the external surface of the aerial vehicle and direct at least some of the atmospheric flow into an aperture in the external surface;

a transfer system configured to transfer the at least some of the atmospheric flow from the aperture to a measurement system;

wherein the transfer system further comprises an outgoing coupling pipe connected to the measurement system and configured to transfer the at least some of the atmospheric flow from the measurement system to the enclosure; and the measurement system that is internal to the external surface of the aerial vehicle and configured to measure atmospheric trace gases in the atmospheric flow.

2. The aerial sampler system of claim 1 wherein the measurement system is farther configured to measure water vapor in the atmospheric flow.

3. The aerial sampler system of claim 1 wherein the measurement system comprises:

a temperature sensor configured to measure temperature within the measurement system; and a pressure sensor configured to measure pressure within the measurement system.

4. The aerial sampler system of claim 1 wherein the enclosure comprises an inertial separator configured to converge and diverge the atmospheric flow.

5. The aerial sampler system of claim 1 wherein the enclosure comprises a flow enhancer configured to direct the atmospheric flow.

6. The aerial sampler system of claim 1 wherein the enclosure comprises a pressure sensor configured to determine pressure for ice detection.

7. The aerial sampler system of claim 1 wherein the enclosure comprises electrically heated metal configured to remove ice.

8. The aerial sampler system of claim 1 wherein the transfer system further comprises an incoming coupling pipe configured to transfer the at least some of the atmospheric flow from the aperture to the measurement system.

9. The aerial sampler system of claim 1 wherein the incoming coupling pipe is heated.

10. An aerial sampler system comprising:

an enclosure connected to an external surface of an aerial vehicle and configured to receive atmospheric flow from the external surface of the aerial vehicle and direct at least some of the atmospheric flow into an aperture in the external surface;

a transfer system configured to transfer the at least some of the atmospheric flow from the aperture to a measurement system; and the measurement system that is internal to the external surface of the aerial vehicle and configured to measure atmospheric trace gases in the atmospheric flow;

wherein the measurement system comprises a laser transmitter configured to transmit laser signals;

a receiver configured to receive the laser signals; and a processing system configured to determine water vapor based on the received laser signals.

11. The aerial sampler system of claim 10 wherein the laser transmitter comprises a diode laser transmitter.

12. The aerial sampler system of claim 10 wherein the laser transmitter comprises a quantum cascade laser transmitter.

13. The aerial sampler system of claim 10 wherein a frequency of the laser transmitter is chosen for one of the atmospheric trace gases.

14. The aerial sampler system of claim 10 wherein the measurement system further comprises a reflective material configured to reflect the laser signals.

15. An aerial sampler system comprising:

an enclosure connected to an external surface of an aerial vehicle and configured to receive atmospheric flow from the external surface of the aerial vehicle and direct at least some of the atmospheric flow into an aperture in the external surface;

a transfer system configured to transfer the at least some of the atmospheric flow from the aperture to a measurement system; and the measurement system that is internal to the external surface of the aerial vehicle and configured to measure atmospheric trace gases in the atmospheric flow;

wherein the measurement system comprises a first laser transmitter configured to transmit first laser signals;

a first receiver configured to receive the first laser signals;

a second laser transmitter configured to transmit second laser signals;

a second receiver configured to receive the second laser signals; and a processing system configured to measure gas from a volcanic eruption based on the first received laser signals and determine whether the volcanic aerosol content is high based on the second received laser signals.

16. A method for operating an aerial sampler system, the method comprising:

receiving atmospheric flow from an external surface of an aerial vehicle into an enclosure connected to the external surface of the aerial vehicle;

directing at least some of the atmospheric flow into an aperture in the external surface;

in a transfer system, transferring the at least some of the atmospheric flow from the aperture to a measurement system that is internal to the external surface of the aerial vehicle;

in the transfer system, transferring the at least some of the atmospheric flow from the measurement system to the enclosure; and in the measurement system, measuring atmospheric trace gases in the atmospheric flow.

17. The method of claim 16 further comprising in the measurement system, measuring water vapor in the atmospheric flow.

18. The method of claim 16 further comprising converging and diverging the atmospheric flow with an inertial separator in the enclosure.

19. The method of claim 16 further comprising directing the atmospheric flow with a flow enhancer in the enclosure.

20. The method of claim 16 further comprising in a pressure sensor in the enclosure, determining pressure for ice detection.

21. The method of claim 16 further comprising removing ice with electrically heated metal in the enclosure.

22. A method for operating an aerial sampler system, the method comprising:

receiving atmospheric flow from an external surface of an aerial vehicle into an enclosure connected to the external surface of the aerial vehicle;

directing at least some of the atmospheric flow into an aperture in the external surface;

in a transfer system, transferring the at least some of the atmospheric flow from the aperture to a measurement system that is internal to the external surface of the aerial vehicle; and in the measurement system, measuring atmospheric trace gases in the atmospheric flow;

transmitting laser signals from a laser transmitter in the measurement system;

receiving the laser signals into a receiver in the measurement system; and in a processing system in the measurement system, determining water vapor based on the received laser signals.

23. The method of claim 22 wherein the laser transmitter comprises a diode laser transmitter.

24. The method of claim 22 wherein the laser transmitter comprises a quantum cascade laser transmitter.

25. The method of claim 22 wherein a frequency of the laser transmitter is chosen for one of the atmospheric trace gases.

26. The method of claim 22 further comprising reflecting the laser signals with a reflective material in the measurement system.

27. The method of claim 22 further comprising:

in a temperature sensor in the measurement system, measuring temperature within the measurement system; and in a pressure sensor in the measurement system, measuring pressure within the measurement system.

28. A method for operating an aerial sampler system the method comprising:

receiving atmospheric flow from an external surface of an aerial vehicle into an enclosure connected to the external surface of the aerial vehicle;

directing at least some of the atmospheric flow into an aperture in the external surface;

in a transfer system, transferring the at least some of the atmospheric flow from the aperture to a measurement system that is internal to the external surface of the aerial vehicle; and in the measurement system measuring atmospheric the gases in the atmospheric flow;

transmitting first laser signals from a first laser transmitter in the measurement system;

receiving the first laser signals into a first receiver in the measurement system;

transmitting second laser signals from a second laser transmitter in the measurement system;

receiving the second laser signals into a second receiver in the measurement system; and in a processing system, measuring gas from a volcanic eruption based on the first received laser signals; and in the processing system, determining whether the volcanic aerosol content is high based on the second received laser signals.

* * * * *